United States Patent [19]
van't Riet et al.

[11] 4,263,322
[45] Apr. 21, 1981

[54] HYDROXY BENZOHYDROXAMIC ACIDS AND BENZAMIDES

[76] Inventors: Bartholomeus van't Riet, 3419 Noble Ave., Richmond, Va. 23222; Howard L. Elford, 3313 Gloucester Rd., Richmond, Va. 23227; Galen L. Wampler, 6938 Chamberlayne Rd., Mechanicsville, Va. 23111

[21] Appl. No.: 16,472

[22] Filed: Mar. 1, 1979

[51] Int. Cl.³ ............... C07C 103/26; C07C 131/11; A61K 31/165
[52] U.S. Cl. ...................... 424/324; 260/500.5 H; 424/315; 424/317; 424/320; 424/327; 564/177
[58] Field of Search ........ 260/559 R, 559 S, 500.5 H; 424/317, 315, 324

[56] References Cited
U.S. PATENT DOCUMENTS
2,849,480  8/1958  Kreuchunes ............... 260/559 S X OTHER PUBLICATIONS
Gale et al., CA 76:21107z (1972).
Howle et al., CA 71:57006b (1969).
Gasparini et al., CA 74:112752f (1971).
Hasui et al., CA 81:120190f (1974).
Yasuda et al., CA 85:94115w (1976).

Primary Examiner—Thomas A. Waltz
Attorney, Agent, or Firm—James L. Rowe; Arthur R. Whale

[57] ABSTRACT

Di or trihydroxybenzohydroxamic acids or N-substituted benzamides, inhibitors or ribonucleotide reductase.

3 Claims, No Drawings

HYDROXY BENZOHYDROXAMIC ACIDS AND BENZAMIDES

This invention provides di and trihydroxybenzohydroxamic acid of the formula

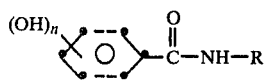

wherein n is 2 or 3 and R is OH or $(C_1-C_3)$alkyl. The term $(C_1-C_3)$alkyl includes methyl, ethyl, n-propyl and isopropyl. A preferred group of compounds are those in which at least two of the hydroxy groups in the phenyl ring of the benzohydroxamic acid are vicinal; i.e. hydroxy groups occupying adjacent carbons, carbons 2 and 3 or 3 and 4 of the phenyl ring. Illustrative compounds coming within the scope of this invention include:
2,4,6-trihydroxybenzohydroxamic acid;
2,4-dihydroxybenzohydroxamic acid;
2,5-dihydroxybenzohydroxamic acid;
N-ethyl 3,5-dihydroxybenzamide.

Compound of this invention with vicinal hydroxy include in addition
2,3,4-trihydroxybenzohydroxamic acid;
3,4,5-trihydroxybenzohydroxamic acid;
2,3,5-trihydroxybenzohydroxamic acid;
2,4,5-trihydroxybenzohydroxamic acid;
2,3,6-trihydroxybenzohydroxamic acid;
2,3-dihydroxybenzohydroxamic acid;
3,4-dihydroxybenzohydroxamic acid;
N-methyl 2,3,4-trihydroxybenzamide;
N-ethyl 3,4,5-trihydroxybenzamide;
N-n-propyl 3,4-dihydroxybenzamide;
and the like.

In another aspect of this invention there is provided a method of inhibiting the enzyme ribonucleotide reductase which comprises administering to a mammal carrying a tumor having a relatively high ribonucleotide reductase level an amount of a compound according to formula II below effective to inhibit ribonucleotide reductase

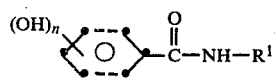

wherein $R^1$ is H, OH or $(C_1-C_3)$alkyl and n is 2 or 3. As before, we prefer to use as ribonucleotide reductase inhibitors in our novel method compounds according to II in which at least two of the hydroxyls are vicinal.

Illustrative compounds useful in our novel method include, in addition to the polyhydroxy hydroxamic acids and N-alkyl benzamides listed above, the following benzamides:
3,4-dihydrobenzamide;
2,3-dihydroxybenzamide;
2,3,4-trihydroxybenzamide;
3,4,5-trihydroxybenzamide;
2,4,5-tri-hydroxybenzamide;
2,3,6-trihydroxybenzamide;
and the like.

The novel compounds of this invention according to formula I above in which R is OH, are prepared by reacting the corresponding ester with hydroxylamine in the presence of sodium hydroxide and sodium sulfite.

The following examples illustrate the preparation of hydroxamic acids of this invention.

EXAMPLE 1

Preparation of hydroxbenzohydroxamic acid

One-half mol of sodium hydroxide as a 25% aqueous solution was added slowly to a mixture of 0.1 mol of hydroxylamine sulfate $[(NH_2OH)_2.H_2SO_4]$ and 100 g. of ice. Next 2 g. of sodium sulfite and 0.1 mol of the particular methyl (hydroxy substituted)benzoate were added. The reaction was stirred at room temperature in a covered flask until the ester dissolved. It was then allowed to remain overnight at 45° C. (or for two days at ambient temperature). The reaction mixture was acidified with 25% aqueous sulfuric acid to pH=6.0 with external cooling. Frequently, part of the hydroxamic acid prepared in the above procedure precipitiated at this point. However, in all instances, the aqueous solvent was evaporated under reduced pressure and the residue extracted with hot methanol and filtered. Evaporation of the methanol left the hydroxamic acid as a residue. This residue was combined with the initial precipitate and the combined hydroxamic acids decolorized with charcoal and then recrystallized from hot water.

The following table gives the physical constants of several hydroxybenzohydroxamic acids prepared by the above procedure.

TABLE 1

| Name of Compound | M.P. °C. |
| --- | --- |
| 2,3-dihydroxybenzohydroxamic acid[a] | 218 dec |
| 2,4-dihydroxybenzohydroxamic acid[a] | 178 dec |
| 2,5-dihydroxybenzohydroxamic acid[a] | 216 dec |
| 2,6-dihydroxybenzohydroxamic acid[a] | 215 dec |
| 3,4-dihydroxybenzohydroxamic acid[c] | 174 dec |
| 3,5-dihydroxybenzohydroxamic acid[a] | 230 dec |
| 2,3,4-trihydroxybenzohydroxamic acid[b] | 201 dec |
| 3,4,5-trihydroxybenzohydroxamic acid[a] | 230 dec |

[a] = recrystallized from $H_2O$
[b] = recrystallized from $H_2O$—MeOH
[c] = recrystallized from ethanol-ethyl acetate
dec = with decomposition Preparation of starting materials The di and trihydroxybenzoic acid esters employed as starting materials in the above procedure were themselves prepared from the corresponding di or trihydroxybenzoic acid according to the following procedure: one-tenth mol of the di or trihydroxybenzoic acid was refluxed for about 24 hours with 100 ml. of methanol containing 2% (v/v) concentrated sulfuric acid. After the reflux period had ended, the excess methanol was removed by evaporation under reduced pressure and the residual esters suspended in water. The esters was isolated therefrom by published procedures. The following di or trihydroxybenzoic acid methyl esters are known: 2,3-dihydroxy, 2,5-dihydroxy, 3,4-dihydroxy, 3,4,5-trihydroxy.

2,3,4-Trihydroxybenzoic acid was not commercially available, but was readily prepared by heating pyrogallol with sodium bicarbonate (20 g. to 30 g.) in a mixture of 30 ml. of water and 20 ml. of mesitylene. Acidification of the resulting suspension with aqueous concentrated hydrochloric acid yielded 2,3,4-trihydroxybenzoic acid melting at about 220° C. with decomposition, a melting point quite in line with the literature melting point of 221° C. Methyl 2,3,4-trihydroxybenzoate was prepared by heating the acid with a methanol-sulfuric acid mixture. The compound thus prepared melted 151° C. compared to a literature melting point of 153° C. The methyl ester of 2,6-dihydroxybenzoic acid was synthesized by preparing the silver salt of the acid and treating it with methyl iodide. Methyl 2,6-dihydroxybenzoic melted at 67° C., a good correspondence with the published melting point of 67°–68° C.

The N-substituted benzamides of this invention are prepared according to the procedure of Example 1 except that methylamine, ethylamine, n-propylmaine, or isopropylamine is substituted for hydroxylamine sulfate in the reaction. Similarly the unsubstituted benzamides, those compounds occurring in formula II in which $R^1$ is H useful in the novel method of this invention, are prepared by reacting the given ester with ammonia in a sealed reaction vessel. The unsubstituted benzamides are, in general, known compounds.

As stated above the compound of the invention represented by formula I above have the ability to inhibit ribonucleotide reductase, an enzyme involved in the reductive conversion of ribonucleotides to deoxyribonucleotides. This reaction is a rate controlling step in the biosynthetic pathway leading to DNA and cell replication. In general, the ribonucleotide reductase level is closely correlated with cellular replication. Thus, it is not surprising that the compounds of this invention, which are potent ribonucleotide reductase inhibitors, are also capable of prolonging the life of mice carrying transplanted tumors. In particular, we have found that administration of compound of this invention and those closely related hydroxybenzamides, all of which compounds which are represented by formula II above, have demonstrated an ability to prolong the life mice inoculated with L1210 leukemia, a tumor not ordinarily susceptible to chemotherapy. Table 2 which follows gives some biological data for compounds of this invention. In the table, column 1 gives the substitution pattern in the benzene ring of the hydroxamic acid, column 2 the substituent, if any, on the benzamide nitrogen, column 3, the $ID_{50}$ (inhibitory dose in millimoles which inhibits ribonucleotide reductase by 50%), column 4 the average percent ($\pm$ standard error) increase in the life span of 8 treated mice compared with 8 control mice at the dose level indicated in column 5 for a period of eight days. Table 3 gives the relative potency of the compounds represented by formula II above as inhibitors of ribonucleotide reductase giving hydroxy urea a value of 1.0. In Table 3, column 1 gives the name of the compound and column 2 the relative inhibitory potency of each of the compounds of column 1.

TABLE 2

$$(OH)_n \underset{\longleftarrow}{\overset{\displaystyle \bigcirc}{\phantom{x}}} \overset{\displaystyle O}{\underset{\displaystyle \|}{C}} -NH-R^1$$

| $(OH)_n$ | $R^1$ | $ID_{50}(\mu M)$ | T/C % | Dose mg/kg |
|---|---|---|---|---|
| 2,3 | OH | 8 | 136 ± 11 | 200 |
| 2,4 | OH | 250 | 142 ± 7 | 500 |
| 2,5 | OH | 200 | 130 ± 14 | 300 |
| 2,6 | OH | 100 | Not tested | Not tested |
| 3,4 | OH | 30 | 203 ± 15 | 600 |
| 3,5 | OH | 400 | 152 ± 22 | 1000 |
| 2,3,4 | OH | 3.5 | 130 ± 7 | 125 |
| 3,4,5 | OH | 10 | 153 ± 19 | 500 |
| 3,4 | H | 50 | 135 ± 11 | 1200 |
| 2,3,4 | H | 5 | 148 ± 7 | 200 |
| 3,4,5 | H | 10 | 142 ± 5 | 250 |
| 3,4,5 | $CH_3$ | 25 | Not tested | Not tested |

TABLE 3

| Name of compound | Inhibitory Potency for ribonucleotide reductase |
|---|---|
| Hydroxy urea | 1.0 |
| 3,5-dihydrobenzohydroxamic acid | 1.2 |
| 2,4-dihydroxybenzohydroxamic acid | 2.0 |
| 2,5-dihydroxybenzohydroxamic acid | 2.5 |
| 2,6-dihydroxybenzohydroxamic acid | 5.0 |
| Vicinal hydroxyls | |
| 2,3-dihydroxybenzodroxamic acid | 63 |
| 3,4-dihydroxybenzohydroxamic acid | 20 |
| 3,4-dihydroxybenzamide | 25 |
| 3,4,5-trihydroxybenzohydroxamic acid | 50 |
| 2,3,4-trihydroxybenzohydroxamic acid | 167 |
| 3,4,5-trihydroxybenzamide | 50 |
| 2,3,4-trihydroxybenzamide | 100 |

In addition, the compounds represented by formula II have shown activity against transplanted tumors in mice using a slightly different protocol from that set forth above. For example 3,4,5-trihydroxybenzohydroxamic acid demonstrated a slight prolongation of life against X5563 at dose levels of 100 mg./kg. twice a day for ten days by intraperitoneal route. Against adenocarcinoma 775, 3,4,5-trihydroxybenzamide when administered at a rate of 200 mg./kg. twice a day for ten days by the intraperitoneal route again gave a slight percentage inhibition. 3,4,5-Trihydroxybenzohydroxamic acid also gave a slight prolongation of life (statistically significant) in the Lewis Lung tumor at a dose level of 100 mg./kg. twice a day for ten days by the intraperitoneal route. Several of the compounds gave good to excellent prolongation of life in L1210 leukamia. For example, 3,4-dihydroxybenzohydroxamic acid at a dose level of 200 mg./kg. twice a day for ten days provided a 141% prolongation and 3,4,5-hydroxybenzamide a prolongation of a 108% for the same dose regimen.

In the above determination of $ID_{50}$'s in Table 2 ribonucleotide reductase is partially purified from Novikoff hepatoma by a procedure similar to that set forth by Elford et al. *J. Biol. Chem.* 245, 5228 (1970). The activity of the enzyme was measured by a slightly modified assay procedure originally developed by Reichard et al. ibid, 236, 1150 (1969). This procedure measures the conversion of CDP to dCDP. The assay mixture (0.34 ml.) contains 3 $\mu$Ci of [$^3$H] CDP (specific acitivity 14–19 Ci/$\mu$mol), 3,3 $\mu$mole ATP, 5.9 $\mu$moles magnesium chloride, 8.8 $\mu$moles Hepes buffer at pH=7.5, 15 $\mu$moles dithiothreitol and enzyme protein between 0.4 and 1.3 mg. Incubation was provided for forty minutes at 30° C. The inhibitors were dissolved in water and a mixture of water and up to 1% ethanol or 2% dimethylsulfoxide, neither one of which were inhibitory of the enzyme at these concentrations. Each inhibitor was tested at a minimum of three concentrations and the active compounds reassayed at least one additional time. $ID_{50}$'s in $\mu$moles were estimated from graphs summarizing results for each compound.

The in vivo L1210 leukemia test involved the transplation of cells propagated in DBA/2 mice.

We claim:

1. A method of inhibiting ribonucleotide reductase which comprises administering to a mammal carrying a tumor having a relatively high ribonucleotide reductase level, an amount of a compound according to the following formula effective to inhibit ribonucleotide reductase

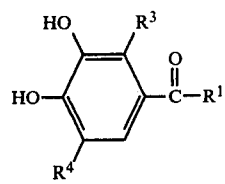
wherein $R^3$ and $R^4$ are H or OH and $R^1$ is $NH_2$ or NHOH such that, when $R^1$ is $NH_2$, $R^3$ is H and $R^4$ OH and when $R^1$ is NHOH, $R^3$ is OH and $R^4$ is H.
2. A method according to claim 1 in which 3,4,5-trihydroxybenzamide is administered.
3. A method according to claim 1 in which 2,3,4-trihydroxybenzohydroxamic acid is the active inhibitory drug.
* * * * *